United States Patent
Lizzi et al.

(10) Patent No.: US 6,726,627 B1
(45) Date of Patent: Apr. 27, 2004

(54) SYSTEM AND METHOD FOR ULTRASONIC HARMONIC IMAGING FOR THERAPY GUIDANCE AND MONITORING

(75) Inventors: Frederic Louis Lizzi, Tenafly, NJ (US); Cheri Xiaoyu Deng, Edison, NJ (US)

(73) Assignee: Riverside Research Institute, New York, NY (US)

( * ) Notice: Subject to any disclaimer, the term of this patent is extended or adjusted under 35 U.S.C. 154(b) by 0 days.

(21) Appl. No.: 10/350,994

(22) Filed: Jan. 24, 2003

Related U.S. Application Data

(62) Division of application No. 09/634,272, filed on Aug. 8, 2000, now Pat. No. 6,533,726.
(60) Provisional application No. 60/147,769, filed on Aug. 9, 1999.

(51) Int. Cl.[7] ................................................ A61B 17/22
(52) U.S. Cl. ......................... 600/439; 600/443; 601/2; 601/3; 310/336
(58) Field of Search ................................ 600/439, 443, 600/447, 459; 601/2–4; 310/311, 322, 334, 337, 365, 366

(56) References Cited

U.S. PATENT DOCUMENTS

| | | |
|---|---|---|
| 4,858,124 A | 8/1989 | Lizzi et al. |
| 4,932,414 A | 6/1990 | Coleman et al. |
| 5,733,527 A | 3/1998 | Schutt |
| 5,746,209 A | 5/1998 | Yost et al. |
| 5,769,790 A | 6/1998 | Watkins et al. |

OTHER PUBLICATIONS

C. X. Deng et al., "Imaging and Spectrum Analysis of Contrast Agents in the In Vivo Rabbit Eye Using Very–High–Frequency Ultrasound", Ultrasound in Med. & Biol., vol. 24, No. 3, pp. 383–394, 1998.

*Primary Examiner*—Quang T. Van
(74) *Attorney, Agent, or Firm*—Baker Botts LLP

(57) ABSTRACT

An ultrasound system is provided which includes a therapy ultrasound transducer and a diagnostic ultrasound transducer and operates in accordance with a method to direct the application of the therapy ultrasound. The method includes operating the diagnostic ultrasound transducer to acquire a first ultrasound image; simultaneously operating the diagnostic ultrasound transducer and therapy ultrasound transducer for a second interval to acquire a second ultrasound image; and determining a difference in the first and second images indicative of the pattern of the therapy ultrasound transducer signal. The difference in the images, which result from enhanced non-linearities and propagation distortions induced by the high intensity therapy ultrasound, can be obtained by subtracting the two images. A method is also provided for monitoring the progress of high intensity therapy ultrasound which evaluates transient changes due to in-situ heating as well as permanent changes which result from cell microstructure alteration.

8 Claims, 3 Drawing Sheets

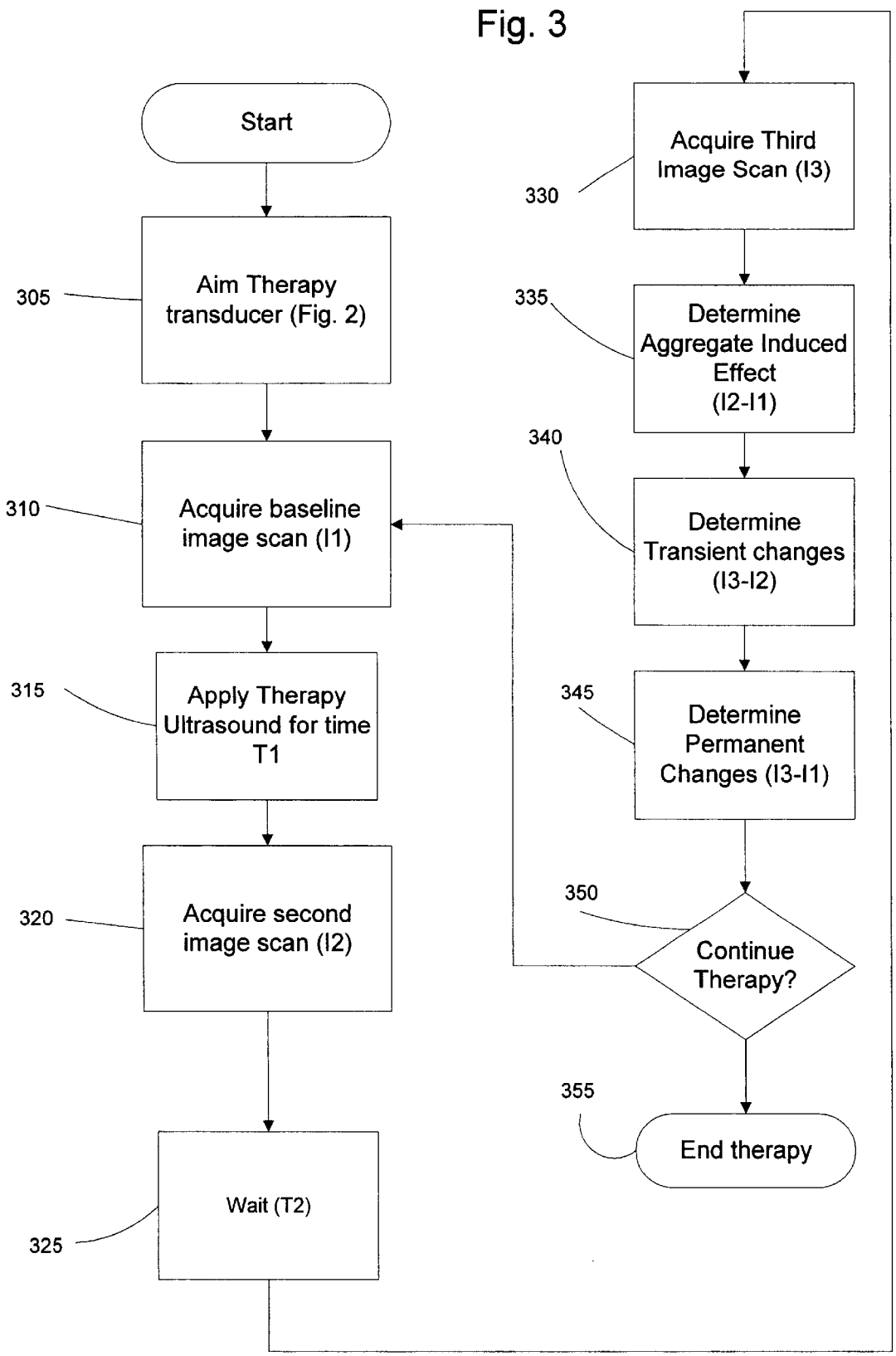

SYSTEM AND METHOD FOR ULTRASONIC HARMONIC IMAGING FOR THERAPY GUIDANCE AND MONITORING

SPECIFICATION

This application is a divisional application of U.S. patent application Ser. No. 09/634,272 entitled SYSTEM AND METHOD FOR ULTRASONIC HARMONIC IMAGING FOR THERAPY GUIDANCE AND MONITORING, which was filed on Aug. 8, 2000 now U.S. Pat. No. 6,533,726 and claims the benefit of U.S. Provisional Application Ser. No. 60/147,769, filed on Aug. 9, 1999.

FIELD OF THE INVENTION

The present invention relates generally to ultrasonic imaging and more particularly relates to the use of harmonic imaging to guide and monitor the application of therapeutic ultrasound.

BACKGROUND OF THE INVENTION

It is known in the art of medical imaging and therapy that ultrasonic energy can be used for both diagnostic purposes and therapeutic purposes. For example, high-intensity focused ultrasound (HIFU) beams can be used to treat tumors by causing local focal temperature increases that cause cell necrosis. In using HIFU, the location of the focused ultrasound beam must be determined to place the beams focal point on the tissue (tumor) which is targeted for therapy. In addition, it is desirable to sense and monitor changes which are induced by the HIFU beam within the exposed tissue.

It is known that non-linear propagation occurs in a medium, such as tissue, which is exposed to intense ultrasound pressure, such as that which occurs from a HIFU beam. The HIFU beam is a high intensity pressure wave which alternately compresses and relaxes the tissue during a signal cycle. As a beam propagates, regions of compression can disturb local propagation speeds and result in regions of increased speeds in compression segments and decreased propagation speeds in rarefaction segments of the wave. This effect locally increases with increasing peak pressure values and also exhibits a cumulative nature, i.e., becoming more prominent as an intense beam propagates further into a medium. This tends to distort the propagating pressure wave and enhance non-linearities in the echo signal. This results in a generation of higher-order harmonics and mixing products in a propagating ultrasound signal. This process is altered, however, by attenuation losses in tissue, which typically increase with increasing frequency.

The use of harmonic imaging in diagnostic imaging is also known in the prior art. However, such systems have been generally used to image non-linear scattering from small, gas-filled contrast agent particles. An example of this can be found in applicants' copending application, Ser. No. 09/318,882, filed on May 26, 1999 and entitled, "Ultrasonic Systems and Methods for Fluid Perfusion and Flow Rate Measurement," which is hereby incorporated by reference. There are also reports that different tissues exhibit different non-linear properties that can be observed in second-harmonic images if the peak pressures of the launched pulse are sufficiently large.

Although harmonic imaging techniques have been evaluated and the non-linear properties of tissues have been observed in the past, these effects have not been used in an advantageous matter to guide and monitor the progress of therapeutic ultrasound.

SUMMARY OF THE INVENTION

It is an object of the present invention to provide a system and method for aiming a therapy ultrasound beam.

It is a further object of the present invention to provide a system and method for monitoring the application of a therapy ultrasound beam using harmonic imaging.

It is another object of the present invention to provide a system and method for detecting thermal lesions resulting from the application of therapeutic ultrasound and determining the position of such lesions using ultrasound harmonic imaging.

A present method is used for aiming or directing a focused ultrasonic therapy beam. The method begins by acquiring a first image scan using a first frequency ultrasound signal. A second image scan is then acquired using the first frequency ultrasound signal in the presence of a therapy beam ultrasound signal. Difference properties in the first and second image scans are then identified to determine where the focused ultrasonic therapy beam is currently directed. The difference properties can be obtained by generating a difference image from the first image and second image scans. The difference image can then be superimposed on the first image scan and displayed to illustrate the presence of the focused ultrasonic therapy beam.

Preferably, the method described is used in conjunction with an ultrasound system which includes a diagnostic ultrasound transducer and a high intensity focused ultrasound therapy transducer which are arranged in a collinear fashion. It is also preferred that the image scans take the form of non-linearity imaging scans, such as harmonic imaging or pulse inversion imaging.

A further method is provided for operating an ultrasound therapy system having a therapy ultrasound transducer and a diagnostic ultrasound transducer to direct the application of the therapy ultrasound. The method includes operating the diagnostic ultrasound transducer for a first interval to acquire a first ultrasound image scan; simultaneously operating the diagnostic ultrasound transducer and therapy ultrasound transducer for a second interval to acquire a second ultrasound image scan; and determining a difference in the first and second image scans indicative of the pattern of the therapy ultrasound transducer signal.

A method of monitoring ultrasound therapy is also provided. This method begins by acquiring a first ultrasound image (baseline) of a region subjected to therapy. High intensity ultrasound is then applied to the region for a first time period. A second ultrasound image of the region is then acquired after the first time period. An aggregate induced effect can be determined based on the first and second image scans. The high intensity ultrasound can then be discontinued for a second time period and a third ultrasound image is then acquired. Transient changes due to in-situ heating in the region and permanent changes due to alteration in tissue microstructure in the region can then be determined.

Generally, the first time period is selected to be long enough such that the applied high intensity ultrasound has a therapeutic effect. The second time period is selected to allow cooling of the region undergoing high intensity ultrasound therapy.

BRIEF DESCRIPTION OF THE DRAWING

Further objects, features and advantages of the invention will become apparent from the following detailed description taken in conjunction with the accompanying figures showing illustrative embodiments of the invention, in which

FIG. 3 is a flow chart illustrating a method of monitoring the application of ultrasound therapy by detecting both transient and permanent changes in a region undergoing ultrasound therapy.

Figure 1:
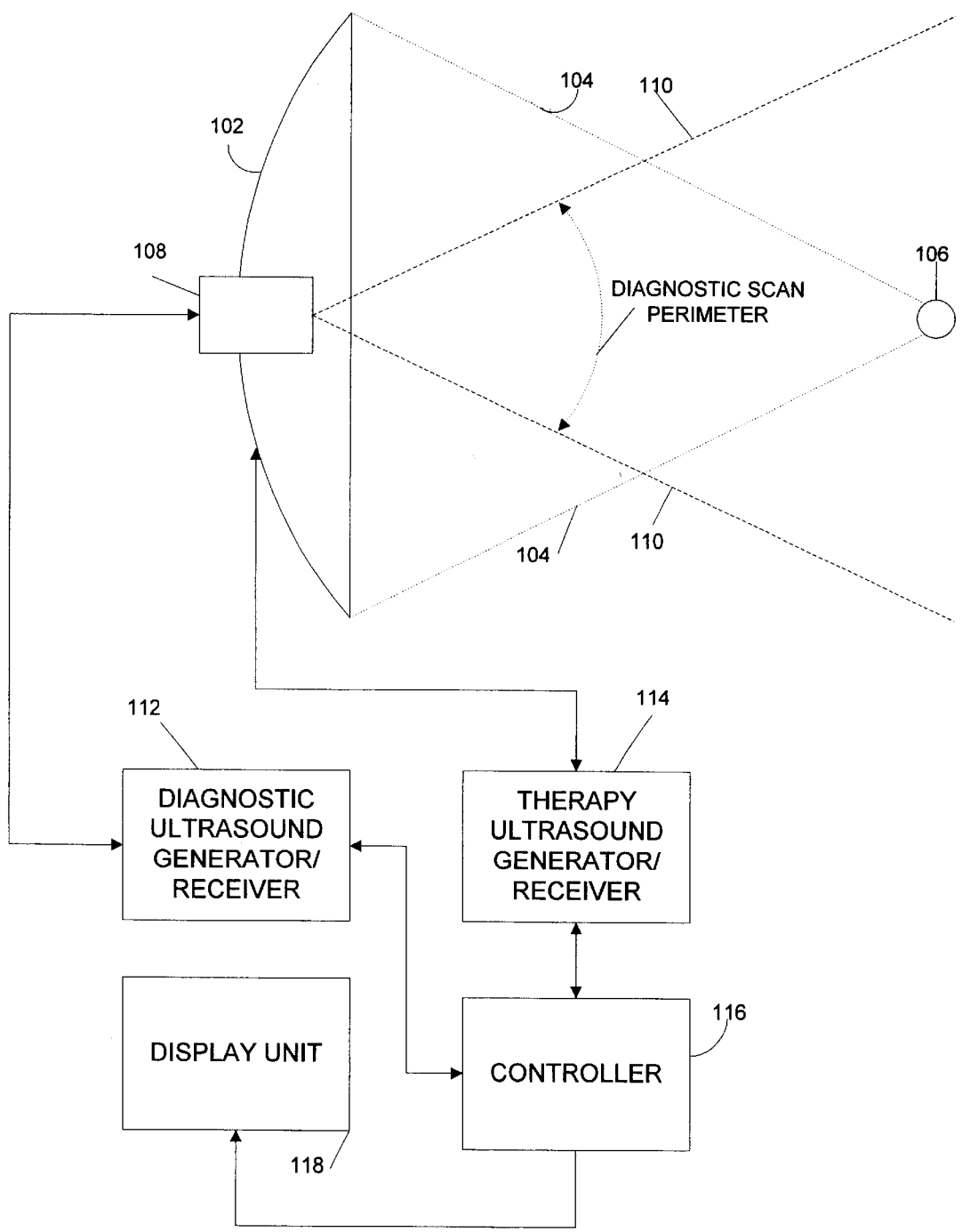
FIG. 1 is a block diagram of an ultrasound therapy system having a collinear therapy ultrasound transducer and diagnostic imaging ultrasound transducer.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

The systems and methods described herein advantageously use signal processing techniques to enhance the detection of non-linear properties of regions undergoing ultrasound diagnostics or therapy. The term non-linearity imaging is used to broadly refer such techniques, which include, without limitation, harmonic imaging and pulse inversion imaging and the like. Throughout the disclosure, embodiments are described in the context of harmonic imaging. However, this is only intended to be one exemplary manner of performing non-linearity imaging.

FIG. 1 is a simplified block diagram of the present ultrasound diagnostic and therapy system. The system includes a therapy ultrasound transducer 102 for generating a therapy beam 104 which is focused to an apex referred to as the therapy beam focal point 106. The therapy beam 104 is generally a high-intensity focused ultrasound (HIFU) beam. The system also includes a diagnostic ultrasound transducer or array 108 which can scan a region 108 with an ultrasound signal suitable for image acquisition. Scanning of this type is known and can be performed by physically directing the position of a transducer or by altering the propagation characteristics of the array 108. Preferably, the diagnostic ultrasound transducer 108 is arranged in a collinear manner with respect to the therapy ultrasound transducer 102. It is possible for the diagnostic ultrasound transducer 108 to be a receive only device. In such a case, the diagnostic ultrasound transducer would receive and process harmonic echo signals resulting from the incident signal from the therapy ultrasound transducer.

The transducers are coupled to appropriate ultrasound generators/receivers 112, 114 respectively, which are operatively coupled to a system controller 116. The system controller is also coupled to a display unit 118. These system components are well known in the art of ultrasound imaging and therapy. A General Electric Logiq 700 MR ultrasound unit which provides conventional B-mode (brightness mode) images and harmonic ultrasound images is suitable for practicing the present invention.

Figure 2:
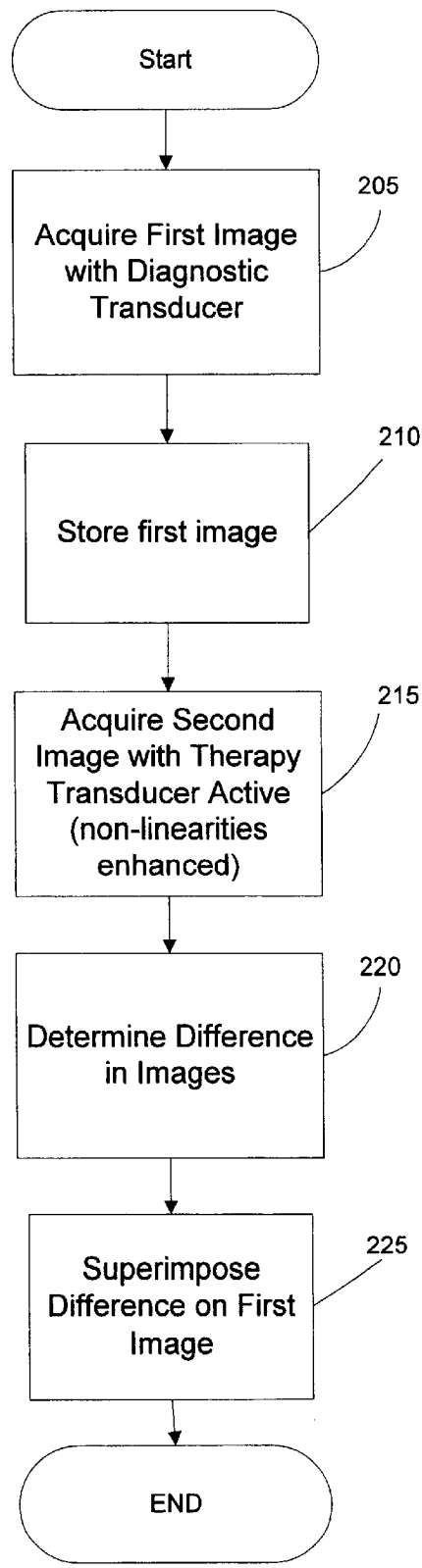
FIG. 2 is a flow chart illustrating a method of operating the system of FIG. 1 to aim a therapy transducer to a targeted region.

FIG. 2 is a flow chart illustrating a process for aiming the system of FIG. 1 prior to application of therapeutic ultrasound from the therapy ultrasound transducer 102. First, with the therapy ultrasound transducer 102 inactive, a cross section image scan is obtained using the diagnostic ultrasound transducer 108 (step 205). This image scan data is stored (step 210). The image scan data can be stored as acquired echo data, post-processed image data (pixels) or some intermediate data form. Next, the therapy ultrasound transducer 102 is activated to generate a brief pulse of ultrasound with a large peak-pressure while a signal from the diagnostic ultrasound transducer is also applied to acquire a second image data scan (step 215). The second image data scan is a non-linear imaging scan, such as harmonic imaging. The pulse from the therapy ultrasound transducer 102 is short enough such that no therapeutic tissue alteration results, such as heating or necrosis.

The ultrasound excitation from the therapy ultrasound transducer 102 enhances the non-linear phenomena in the tissue and when the signals from the therapy ultrasound transducer 102 and diagnostic transducer combine, this results in the generation of enhanced mixing products as well as second, and higher order, harmonics. If, for example, the diagnostic transducer is operating in a frequency band centered about f1 and the therapy transducer is operating in a band centered about f2, the non-linearities induced in the tissue would result in mixing products f1+f2, f1−f2 as well as harmonic components n*f1 and n*f2, where n is an integer greater than 1. This results from the compression of tissue during the high-pressure portions of the cycle and tissue relaxation during the low pressure cycles of the therapy ultrasound signal which alter the propagation properties of the tissue. These effects vary depending on the peak pressure value applied. Thus, the first image and second image will differ in regions that experience simultaneous presence of the therapy beam and diagnostic beam, whose pressures are coherently additive.

During acquisition of the second image scan, the therapy ultrasound signal and the diagnostic ultrasound signal are temporally coexistent. Generally, the therapy pulse is lower in frequency than the diagnostic pulse. Therefore, the coexistence can occur by superimposing the high frequency diagnostic pulse on a portion of the lower frequency therapy ultrasound pulse. Preferably, the high frequency diagnostic signal is phase-synchronous with the diagnostic therapy signal such that imaging takes place at defined portions of the therapy ultrasound signal. As the diagnostic ultrasound signal is scanned across the region where the therapy ultrasound signal is present, the harmonic image will detect the areas where the signals coincide. Alternatively, the diagnostic ultrasound transducer can take the form of a receive only transducer which is scanned across the region to detect harmonic components of the therapy ultrasound signal only.

The difference between the first image scan and second image scan can be determined by subtracting the two image scans (step 220). The difference image data can be digitally enhanced by the controller 116 using conventional digital signal processing techniques and then superimposed on the first image to indicate the position of the therapy ultrasound signal 104 and focal point 106 (step 225). If the therapy beam is not in the desired position, the system can be re-aimed and the process can be repeated from step 205. Once the therapy ultrasound signal 104 is properly aimed, the therapy ultrasound signal 104 can be applied for longer durations to induce necrosis of the targeted region.

In some cases, the resulting non-linearities from the coincidental diagnostic ultrasound signal and therapy ultrasound signal will be sufficiently pronounced such that the region occupied by the therapy ultrasound signal 104 will be apparent in the image data scan acquired when the two signals are so applied. In this case, the method of aiming the therapy ultrasound transducer can be performed in a single step of simultaneously operating the diagnostic ultrasound transducer 108 and therapy ultrasound transducer 102 and viewing the resulting non-linearity image.

The system of FIG. 1 can also be used to monitor the progress of induced tissue alteration resulting from the application of the therapy ultrasound beam 104 by detecting changes in the degree of non-linearity in the tissue, referred to herein as the B/A coefficient or non-linearity coefficient. Under the influence of the therapy ultrasound beam, transient changes in the non-linear properties of the tissue arise as a result of in-situ temperature changes, and permanent changes in the non-linear properties of the tissue arise from changes in the tissue microstructure. The in-situ temperature changes are transitory, with the temperature returning to pre-exposure levels as the tissue cools following therapy exposure. Permanent changes in the tissue microstructure result from cell necrosis or other effects, such as cavitation, which result from application of the HIFU beam. Thus, measurement of transient changes can indicate both the degree and spatial extent of induced heating and measurements of permanent changes are indicative of the degree and extent of thermal lesions.

FIG. 3 is a flow chart illustrating a method of determining in-situ heating and tissue alteration using progressive image evaluation. Optionally, the process of aiming the therapy beam set forth in FIG. 2 can be applied to locate the therapy beam 104 (step 305). The therapy ultrasound beam 104 is then activated and baseline image scan data (I1) is acquired using the diagnostic ultrasound array 108 (step 310). Therapy is continued for a time interval (T1) (step 315) and second image scan data (I2) is then acquired (step 320). The therapy transducer 102 can be deactivated for a second time interval (T2) (step 325). The purpose of the second time interval (T2) is to allow the temporary in-situ heating effect to dissipate. This period will vary depending on the power of the applied therapy ultrasound, the duration of the therapy, the nature of the tissue and the depth of the area being treated, among other variables. However, a time period of about 5–10 seconds for T2 is considered reasonable to allow sufficient cooling under various conditions. A third image scan data is then acquired (I3) at the end of the second time interval (step 330). Preferably, to enhance the non-linear effect in the tissue, if the first and second images were acquired with the therapy ultrasound present, the diagnostic transducer is activated along with a brief excitation from the high pressure therapy transducer 102 during acquisition of the third image data.

The aggregate induced effect from the application of the therapy ultrasound signal is apparent from the difference between the second image scan data and the first image scan data (I2−I1) (step 335). From the difference between the third image and the second image (I3−I2), transient effects due to heating can be determined (step 340). From the difference between the third image and the first image (I3−I1), permanent changes due to alterations in the tissue microstructure can be determined (step 345). Once the transient changes and permanent changes are determined, the decision of whether to initiate another therapy beam session is made (step 350), and control reverts to step 310 to continue or to step 355 to end therapy. If the decision is to continue, the application of the therapy ultrasound can be adjusted, if necessary, to alter the in-situ heating detected via the transient changes.

In determining the differences in the image scan data sets, the data can be compared and processed in various forms. The data can be compared as raw echo data, as processed image data (pixels) or some intermediate data processing step.

In the image acquisition operations with respect to FIG. 3, the image acquisition preferably takes place during a intervals when the therapy ultrasound beam is being applied. This is preferred because of the enhanced non-linear effects of having the contemporaneous application of the diagnostic ultrasound and therapy ultrasound signals enhance image acquisition. However, each of the images (I1, I2, I3) can also be acquired with the therapy transducer turned off. In this case, harmonic imaging can still be performed, but with somewhat reduced efficacy.

In the method of FIG. 3, the B/A effects in lesions are measured directly. However, the present systems and methods can also be applied to measure lesions indirectly by using harmonic imaging to evaluate "shadowing" that results from such lesions. Shadowing is a decrease in ultrasound echo strength which causes a concomitant darkening in cross-section ultrasound images. Shadowing results from a relatively high attenuation coefficient in a region of tissue being subjected to ultrasound. The incident ultrasound wave is attenuated when it passes through this region and the reflected wave is again attenuated as the echo signal returns to the transducer. Thus, the echo signal from distal sites behind the tissue causing the shadow is significantly reduced. In general, tissue attenuation coefficients increase with increasing frequency. This not only reduces the intensity of the reflected echo signal, but also reduces the non-linear phenomenon discussed above because the incident pressure of the ultrasound signal is also reduced. Therefore, shadows will be more pronounced when viewed with harmonic images formed using high frequency harmonic components of the ultrasound signal.

The use of HIFU beam therapy can result in thermal lesions. Thermal lesions have an attenuation coefficient which is higher than that of normal tissue. Therefore, shadowing will result from these thermal legions which can be enhanced by the use of harmonic imaging. Further, because shadowing will be manifest behind a lesion but not in front of the lesion, when non-linear imaging is employed, the shadow will generally appear to originate from within the lesion and the lesion location can be readily identified. Thus, by using the diagnostic ultrasound transducer 108 to capture progressive images of a region undergoing therapy ultrasound, and evaluating these images for the occurrence of shadows, the formation of lesions during this process can be readily observed.

The present systems and methods provide a way of effectively aiming a therapy ultrasound transducer to insure that the HIFU beam is properly directed to a targeted area. In addition, once properly aimed, the present systems and methods also provide an effective tool for monitoring the effects of the application of the HIFU beam during therapy.

Although the present invention has been described in connection with specific exemplary embodiments, it should be understood that various changes, substitutions and alterations can be made to the disclosed embodiments without departing from the spirit and scope of the invention as set forth in the appended claims.

What is claimed is:

1. A system for diagnostic imaging and ultrasound therapy, comprising:
   a diagnostic ultrasound transducer;
   a therapy ultrasound transducer;
   a display unit; and
   a controller operatively coupled to the diagnostic ultrasound transducer, the therapy ultrasound transducer and the display unit, the controller:

operating the diagnostic ultrasound transducer to acquire a first non-linearity image scan;

operating the therapy ultrasound transducer to apply a therapy beam ultrasound signal; and operating the diagnostic ultrasound to acquire a second non-linearity image scan;

determining difference properties in the first non-linearity image scan and the second non-linearity image scan to determine an effect from the therapy ultrasound transducer.

2. The system of claim 1, wherein the controller:

generates difference image data from the first non-linearity image scan and the second non-linearity image scan; and superimposes the difference image data on the first non-linearity image scan and displays the superimposed image on the display unit.

3. The system of claim 1, wherein the controller employs digital signal processing to enhance the difference image between said generating and superimposing operations.

4. The system of claim 1, wherein the difference properties are detected by the controller evaluating mixing products of the diagnostic ultrasound transducer signal and the therapy ultrasound transducer signal.

5. The system of claim 1, wherein the difference properties are detected by the controller evaluating harmonic components of the diagnostic ultrasound transducer signal.

6. The system of claim 1, wherein the difference properties are detected by the controller evaluating harmonic components of the therapy ultrasound transducer signal.

7. The system of claim 1, wherein the second non-linearity image scan is acquired during application of the therapy beam ultrasound signal.

8. The system of claim 1, wherein the second non-linearity image scan is acquired after application of the therapy beam ultrasound signal.

* * * * *

UNITED STATES PATENT AND TRADEMARK OFFICE
CERTIFICATE OF CORRECTION

PATENT NO. : 6,726,627 B1
DATED : April 27, 2004
INVENTOR(S) : Lizzi et al.

It is certified that error appears in the above-identified patent and that said Letters Patent is hereby corrected as shown below:

Title page,
Item [56], References Cited, U.S. PATENT DOCUMENTS, should include:
-- 6,042,556   3/28/2000    Beach, et al.
   6,500,141   12/31/2002   Irion, et al. --

Signed and Sealed this

Eighth Day of February, 2005

JON W. DUDAS
*Director of the United States Patent and Trademark Office*